United States Patent [19]

Lippmann

[11] 4,267,189
[45] May 12, 1981

[54] METHOD OF USE AND COMPOSITION FOR 1,3-DIHYDRO-3-(2-HYDROXY-2-METHYL-PROPYL)-2H-ISOINDOL-1-ONE

[75] Inventor: Wilbur Lippmann, St. Laurent, Canada

[73] Assignee: American Home Products Corporation

[21] Appl. No.: 78,548

[22] Filed: Sep. 24, 1979

[51] Int. Cl.$^3$ .............................................. A61K 31/40
[52] U.S. Cl. .................................................. 424/274
[58] Field of Search ......................................... 424/274

[56] References Cited

U.S. PATENT DOCUMENTS 3,892,771  7/1975  Eberle ................................... 424/274
4,021,448  5/1977  Bell ....................................... 424/274

OTHER PUBLICATIONS

Roth et al.–*Arch. Pharm.*, 309, 58 (1976).

*Primary Examiner*—Frederick E. Waddell
*Attorney, Agent, or Firm*—Arthur E. Wilfond

[57] ABSTRACT

Disclosed is pharmaceutical compositions and methods of using 1,3-dihydro-3-(2-hydroxy-2-methylpropyl)-2H-isoindol-1-one for treating ulcers in a mammal and for preventing or decreasing the secretion or availability of excessive amounts of gastric acid in a mammal suffering from hyperchlorhydria and/or associated conditions.

5 Claims, No Drawings ns or solutions, or it can be injected parenterally. The
METHOD OF USE AND COMPOSITION FOR 1,3-DIHYDRO-3-(2-HYDROXY-2-METHYL-PROPYL)-2H-ISOINDOL-1-ONE 1,3-Dihydro-3-(2-hydroxy-2-methylpropyl)-2H-isoindol-1-one is disclosed as an intermediate for the production of TRICYCLIC ISOINDOLE DERIVATIVES in Ser. No. 78,547 of Christopher A. Demerson, Jean-Marie Ferland and Leslie G. Humber, filed on even date herewith, and is referred to as 2,3-dihydro-3-(2-hydroxy-2-methylpropyl)-1H-isoindol-1-one in Example 37 thereof. Application Ser. No. 78,546 of Wilbur Lippmann, Christopher A. Demerson, Leslie G. Humber and Jean-Marie Ferland for 1,3-DIHYDRO-3-(2-HYDROXYETHYL)-2H-ISOINDOL-1-ONE DERIVATIVES, filed on even date herewith, also is related hereto.

BACKGROUND OF THE INVENTION a. Field of the Invention

This invention relates to novel pharmaceutical compositions and methods of using 1,3-dihydro-3-(2-hydroxy-2-methylpropyl)-2H-isoindol-1-one. This compound is useful for treating of ulcers in a mammal and for preventing or decreasing the secretion or availability of excessive amounts of gastric or hydrochloric acid in a mammal suffering from hyperchlorhydria and/or associated conditions.

b. Description of the Prior Art

A search of the chemical literature for 3-substituted derivatives of 1,3-dihydro-2H-isoindol-1-one has revealed the following references: H. J. Roth and G. Hundeskagen, Arch. Pharm., 309, 58 (1976), and M. K. Eberle, U.S. Pat. No. 3,892,771. Although these references disclose a number of 3-substituted 1,3-dihydro-2H-isoindol-1-one compounds, they do not reveal 1,3-dihydro-3-(2-hydroxy-2-methylpropyl)-2H-isoindol-1-one.

SUMMARY OF THE INVENTION 1,3-Dihydro-3-(2-hydroxy-2-methylpropyl)-2H-isoindol-1-one is useful for treating ulcers in a mammal by administering to the mammal an effective ulcer alleviating amount of the latter compound. The compound also is useful for preventing or decreasing the secretion or availability of excessive amounts of gastric acid in a mammal, which comprises administering to the mammal suffering from hyperchlorhydria and/or associated conditions an effective amount of the compound.

1,3-Dihydro-3-(2-hydroxy-2-methylpropyl)-2H-isoindol-1-one forms a pharmaceutical composition for oral or parenteral administration by combining the latter compound with a pharmaceutically acceptable carrier.

DETAILED DESCRIPTION OF THE INVENTION

When 1,3-dihydro-3-(2-hydroxy-2-methylpropyl)-2H-isoindol-1-one is administered to mammals suffering from hyperchlorhydria and/or associated conditions for the purpose of preventing or decreasing the secretion of excessive amounts of gastric acid or is used for the treatment of ulcers in mammals, it is used alone or in combination with pharmacologically acceptable carriers, the proportion of which is determined by the solubility and chemical nature of the compound, chosen route of administration and standard biological practice.

For example, it can be administered orally in solid form, i.e. capsule or tablet, orally in liquid form, i.e. suspensions or solutions, or it can be injected parenterally. The preferred method of administration is orally.

The tablet compositions contain 1,3-dihydro-3-(2-hydroxy-2-methylpropyl)-2H-isoindol-1-one in admixture with nontoxic pharmaceutical excipients, for example, starch, milk, sugar, certain types of clay etc. The tablets can be uncoated or they can be coated by known techniques so as to delay disintegration and adsorption in the gastrointestinal tract and thereby provide a sustained action over a longer period.

The aqueous suspensions for oral administration contain the compound in admixture with one or more nontoxic pharmaceutical excipients known to be suitable in the manufacture of aqueous suspensions. Suitable excipients are, for example, methylcellulose, sodium alginate, gum acacia, lecithin, etc. The aqueous suspensions can also contain one or more preservatives, one or more coloring agents, one or more flavoring agents and one or more sweetening agents.

Non-aqueous suspensions for oral administration can be formulated by suspending the compound in a vegetable oil, for example, arachis oil, olive oil, sesame oil, or coconut oil, or in a mineral oil, for example, liquid paraffin, and the suspension may contain a thickening agent, for example, beeswax, hard paraffin or cetyl alcohol. These compositions can also contain a sweetening agent, flavoring agent or antioxidant.

For administration to a mammal by parenteral injection, it is preferred to use the compound in solution in a sterile aqueous vehicle, which may also contain other solutes such as buffers or preservatives, as well as sufficient quantities of pharmaceutically acceptable salts or of glucose to make the solution isotonic.

The dosage of 1,3-dihydro-3-(2-hydroxy-2-methylpropyl)-2H-isoindol-1-one for combating or preventing hyperchlorhydria, and/or associated conditions, or for the treatment of ulcers in a mammal will vary with the form of administration and the particular compound chosen. Furthermore, it will vary with the particular host as well as the age, weight and condition of the host under treatment as well as with the nature and extent of the symptoms. Generally, treatment is initiated with small dosages substantially less than the optimum dose of the compound. Thereafter, the dosage is increased by small increments until the optimum effect under circumstances is reached. In general, the compound is most desirably administered at a concentration level that will generally afford effective results without causing any harmful or deleterious side effects. For example, an effective anti-ulcer amount or an effective amount for preventing hyperchlorhydria and inhibiting hydrochloric acid secretion of the compound usually ranges from about 1.0 mg to about 200 mg per kg of body weight per day in single or divided dose, although as aforementioned, variations will occur. However, a dosage level that is in the range from about 10 mg to about 100 mg per kg of body weight per day in single or divided dose is employed most desirably in order to achieve effective results.

The effectiveness of 1,3-dihydro-3-(2-hydroxy-2-methylpropyl)-2H-isoindol-1-one as an agent for preventing hyperchlorhydria and inhibiting hydrochloric acid secretion is demonstrated by the use of rats, more especially the Shay rat (see Example 2). The rat is the preferred experimental mammal for demonstrating the activity of agents affecting gastric acid secretion and it has been widely used in experimental medicine for this purpose. For instance, on page 149 in "Pathophysiology of Peptic Ulcer", published by McGill University Press, Montreal, Canada in 1963, Skoryna states that many of the drugs now in use in human medicine for the treatment of peptic ulcer have been evaluated by the Shay rat method. It is recognized by skilled pharmacologists that results obtained in the Shay rat in the evaluation of gastric acid conditions are translatable to results that will be obtained when the same drug is administered to human beings. For the value of the Shay rat in experimental gastroenterology, see also the article by H. Shay et al., Gastroenterology, 26, 906 (1954). This animal is generally recognized as the preferred, or standard, animal for use experimentally in testing drugs used to inhibit gastric acid secretion.

1,3-Dihydro-3-(2-hydroxy-2-methylpropyl)-2H-isoindol-1-one is shown to be useful for treating ulcers in a mammal by inhibiting basal gastric acid secretion in the rat, as described above, and inhibiting indomethacin-induced ulcer formation in the rat according to the method described by Y. H. Lee et al., Arch. Int. Pharmacodyn. Ther., 191, 370 (1971) and cold-resistant-induced ulcer formation in the rat according to the method described by D. A. Brodie and L. S. Valitski Proc. Soc. Exp. Biol. Med., 113, 998 (1963) as modified by E. C. Senay and R. J. Levine Proc. Soc. Exp. Biol. Med., 124, 1221 (1967) when administered orally or parenterally (see Examples 3 and 4). Compounds, which exhibit activity in the above anti-ulcer or antisecretory tests, are regarded as antiulcer agents.

With regard to the formation of ulcers caused by indomethacin, breakdown of mucosal resistance has been suggested to be of importance, see R. Menguy and L. Desbaillets, Amer. J. Dig. Dis., 12, 862 (1967) and D. M. Nicoloff, Arch. Surg., 97, 809 (1968). Furthermore, a possible role of the vagus was considered, see Y. H. Lee et al., Arch. Int. Pharmacodyn. Ther., 191, 370 (1971). Indomethacin induces ulcer formation, while having no effect on gastric acid secretion (Lee et al., cited above). Although the production of excess gastric acid does not appear to be the mechanism by which indomethacin causes ulcer formation, it is probable that in the presence of a reduced mucosal resistance, gastric acid plays an important role in the ulcer formation. As 1,3-dihydro-3-(2-hydroxy-2-methylpropyl)-2H-isoindol-1-one can inhibit gastric acid secretion, it is this type of action that can be significant in the prevention of ulcer formation.

Anticholinergic agents are known to exhibit gastric acid antisecretory and antiulcer activities in the rat, see J. M. Beiler et al., Arch. Int. Pharmacodyn., 153, 139 (1965); W. Lippmann, Prostaglandins, 7, 1 (1974); and A. Robert et al., Digestion, 11, 199 (1974), and are widely employed clinically as antisecretory-antiulcer agents; however, such agents exhibit various side effects, see D. W. Piper et al., Drugs, 10 56 (1975). In this regard, 1,3-dihydro-3-(2-hydroxy-2-methylpropyl)-2H-isoindol-1-one does not exhibit appreciable anticholineric activity (see Example 5). Accordingly, the lack of this latter activity for 1,3-dihydro-3-(2-hydroxy-2-methylpropyl)-2H-isoindol-1-one is a desirable feature of this compound.

The following examples illustrate further this invention.

EXAMPLE 1

Preparation of 1,3-Dihydro-3-(2-hydroxy-2-methylpropyl)-2H-isoindol-1-one

A solution of 1,3-dihydro-3-oxo-2H-isoindole-1-acetic acid (described by F. M. Rowe et al., J. Chem. Soc., 1098 (1936) 130 g, 0.682 mol) in methanol (1300 ml) containing 6.5 g of p-toluenesulfonic acid was refluxed with stirring for 3.5 hr. Most of the methanol was evaporated and the residue was dissolved in chloroform. The solution was washed with 5% aqueous sodium bicarbonate and water, dried and evaporated. The residue (125 g) was crystallized from isopropanol to give methyl 1,3-dihydro-3-oxo-2H-isoindole-1-acetate, mp 136°–138° C.

A solution of the latter compound (7.2 g, 0.035 mol) in 250 ml of tetrahydrofuran was added dropwise to a solution of methyl magnesium iodide (prepared from magnesium, 4.11 g, 0.075 gram-atoms and methyl iodide, 23.8 g, 0.168 mole, in 200 ml of diethyl ether). The reaction was refluxed for 18 hr with stirring, cooled and poured into 350 ml of ice-cold 10% sulfuric acid. The solution was extracted with chloroform and the chloroform extract was washed with 5% aqueous sodium bicarbonate and water, dried and evaporated. The residue was crystallized from benzene to give 1,3-dihydro-3-(2-hydroxy-2-methylpropyl)-2H-isoindol-1-one (4.8 g), mp 122°–123° C., Anal. Calc'd. for $C_{12}H_{15}NO_2$:C, 70.22% H, 7.37% N, 6.82% and Found: C, 70.11% H, 7.37% N, 6.96%.

EXAMPLE 2

Effect of 1,3-Dihydro-3-(2-hydroxy-2-methylpropyl)-2H-isoindol-1-one on Basal Gastric Acid Secretion in the Rat Gastric acid secretion was measured essentially according to the method of H. Shay et al., Gastroenterol., 26, 906 (1954) as described by W. Lippmann, J. Pharm. Pharmacol., 22,568 (1970). Female Sprague Dawley rats (Canadian Breeding Laboratories; 160–180 g) were fasted for 48 hours before pyloric ligation. After the first 24 hours of fasting the animals were given access to 8% sucrose in 0.2% sodium chloride for 8 hours. Water was permitted ad libitum except during the 8 hour access to sucrose and after the drug treatment. The compounds were suspended in water with the aid of one drop of Tween 80 per 7 ml for oral or intraperitoneal administration. The pylorus was ligated under ether anesthesia and the sutured incision was covered with flexible collodion to prevent the animals from ingesting adhering blood. The stomachs were lavaged with 0.9% sodium chloride until the return solution was clear. Four hours after pyloric ligation, the animals were killed with diethyl ether and the gastric contents were collected in centrifuge tubes. The amount of acid in the centrifuged gastric juice was determined by titration against 0.1 N sodium hydroxide in a direct reading pH meter of pH 7.0.

Atropine sulfate was obtained from May and Baker, Ltd.

Student's t test was used in the evaluation of the data. The $ED_{50}$'s were obtained graphically by plotting the percent inhibition of gastric acid secretion versus the logarithm of the dose of the compound.

The results from the above method are given in Tables 1 and 2.

TABLE 1

Effect of 1,3-Dihydro-3-(2-hydroxy-2-methylpropyl)-2H-isoindol-1-one and Atropine On Gastric Acid Secretion: Intraperitoneal Administration

| Drug | Dose (mg/kg, i.p.) | No. of Animals | Gastric Acid Output (μEq/4 hr ± S.E.) | (% Inhibition) | $ED_{50}$ (mg/kg) |
|---|---|---|---|---|---|
| Vehicle | — | 20 | 545 ± 54 | — | |
| Isoindol-1-one[a] | 50 | 16 | 56 ± 12** | 90 | 25 |
| | 25 | 20 | 275 ± 57* | 49 | |
| | 12 | 18 | 448 ± 59 | 18 | |
| Atropine | 1 | 17 | 182 ± 48** | 67 | 0.5 |
| | 0.5 | 16 | 270 ± 37** | 50 | |
| | 0.25 | 17 | 278 ± 38** | 49 | |

Compounds were administered intraperitoneally (0.5 ml) immediately after pyloric ligation and the animals were sacrificed 4 hours after ligation.
[a]1,3-dihydro-3-(2-hydroxy-2-methylpropyl)-2H-isoindol-1-one
**$p<0.001$; *$p<0.01$

TABLE 2

Effect of 1,3-Dihydro-3-(2-hydroxy-2-methylpropyl)-2H-isoindol-1-one and Atropine On Gastric Acid Secretion: Oral Administration

| Drug | Dose (mg/kg, p.o.) | No. of Animals | Gastric Acid Output (μEq/4 hr ± S.E.) | (% Inhibition) | $ED_{50}$ (mg/kg) |
|---|---|---|---|---|---|
| Vehicle | — | 14 | 435 ± 74 | — | |
| Isoindol-1-one[a] | 100 | 8 | 71 ± 19*** | 84 | 28 |
| | 50 | 8 | 154 ± 33** | 65 | |
| | 25 | 8 | 226 ± 48* | 48 | |
| Atropine | 8 | 8 | 186 ± 53 | 57 | 7 |
| | 4 | 7 | 290 ± 60 | 33 | |
| | 2 | 8 | 436 ± 77 | 0 | |

Compounds were administered orally (0.2 ml) one hour before pyloric ligation and the animals were sacrificed 4 hours after ligation.
[a]1,3-dihydro-3-(2-hydroxy-2-methylpropyl)-2H-isoindol-1-one
***$p<0.001$;
**$p<0.01$;
*$p<0.05$

EXAMPLE 3

Effect of 1,3-Dihydro-3-(2-hydroxy-2-methylpropyl)-2H-isoindol-1-one on Indomethacin-Induced Ulcer Formation The method utilized for the production and evaluation of indomethacin-induced ulcer formation was essentially as described by Y. H. Lee et al., Arch. Int. Pharmacodyn. Ther., 191, 370 (1971). Female albino rats (160–165 g; Sprague-Dawley, Canadian Breeding Laboratories), caged individually were fasted 24 hr with free access to water until the start of the experiment. Indomethacin (20 mg/kg, i.p.) was given, the animals sacrificed by cervical dislocation 5 hr later and the number of ulcers present in the glandular portion of the stomach determined. The test compound was administered orally (0.2 ml) 1 hr before the indomethacin. The vehicle employed for the administrations was water containing Tween 80 (1 drop per 7 ml). There were 12–32 animals per group. Results are given in Table 3.

EXAMPLE 4

Effects of 1,3-Dihydro-3-(2-hydroxy-2-methylpropyl)-2H-isoindol-1-one on Cold-Restraint-Induced Ulcer Formation To assess the effects of the test compound on the development of cold-restraint-induced gastric lesions, the method of D. A. Brodie and L. S. Valitski Proc. Soc. Exp. Biol. Med., 113, 998 (1963) as modified by E. C. Senay and R. J. Levine Proc. Soc. Exp. Biol. Med., 124, 1221 (1967) was used. Food was withheld from male albino rats (165–175 g, Sprague-Dawley, Canadian Breeding Laboratories) for 24 hr but water was freely available. The test compound was administered orally (0.2 ml) to the animals (8–24 per group) 30 min before placing the animals into restrainers, the restrainer was made of plexiglass and restricted the movement of the rat to a minimum. The vehicle employed was as described above. The restrainers were placed in a cold environment (4°–7° C.) for 2 hr. The animals were sacrificed by cervical dislocation, the stomachs removed and

TABLE 3

Effect of 1,3-Dihydro-3-(2-hydroxy-2-methylpropyl)-2H-isoindol-1-one on Indomethacin-Induced Ulcer Formation

| Treatment | Dose (mg/kg, p.o.) | No. of Animals | Ulcers Formed (mean ± S.E.) | (% Inhibition) | p | $ED_{50}$ |
|---|---|---|---|---|---|---|
| Vehicle | — | 32 | 9.8 ± 1.2 | — | — | — |
| Isoindol-1-one[a] | 100 | 17 | 1.8 ± 0.6 | 82 | 0.001 | 22 |
| | 50 | 17 | 2.4 ± 0.7 | 75 | 0.001 | |
| | 25 | 17 | 4.9 ± 1.2 | 50 | 0.01 | |
| Atropine | 2 | 12 | 1.5 ± 0.8 | 85 | 0.001 | 1.1 |
| | 1 | 12 | 5.2 ± 1.5 | 47 | 0.02 | |

[a]1,3-dihydro-3-(2-hydroxy-2-methylpropyl)-2H-Isoindol-1-one the number of ulcers in the glandular portion of the stomach determined. Results are given in Table 4.

TABLE 4
Effect of 1,3-Dihydro-3-(2-hydroxy-2-methylpropyl)-2H-isoindol-1-one on Cold-Restraint Ulcer Formation

| Treatment | Dose (mg/kg, p.o.) | No. of Animals | Ulcers Formed (mean ± S.E.) | (% Inhibition) | p | $ED_{50}$ |
|---|---|---|---|---|---|---|
| Vehicle | — | 24 | 6.5 ± 0.9 | — | — | — |
| Isoindol-1-one[a] | 200 | 14 | 2.0 ± 0.8 | 69 | <0.001 | 80 |
|  | 100 | 8 | 2.9 ± 0.5 | 55 | <0.01 |  |
|  | 50 | 8 | 3.9 ± 1.2 | 40 | <0.1 |  |
| Imipramine | 5 | 17 | 1.2 ± 0.4 | 81 | <0.001 | 1.7 |
|  | 2.5 | 16 | 2.1 ± 0.8 | 68 | <0.001 |  |
|  | 1.25 | 8 | 4.1 ± 1.5 | 37 | >0.1 |  |

[a] 1,3-dihydro-3-(2-hydroxy-2-methylpropyl)-2H-isoindol-1-one

EXAMPLE 5

Anticholinergic Ability of 1,3-Dihydro-3-(2-hydroxy-2-methylpropyl)-2H-isoindol-1-one to Antagonize Oxotremorine-Induced Effects Anticholinergic activity was examined in vivo by determining the ability of the compound to antagonize oxotremorine-induced effects according to the method described by P. S. J. Spencer, Life Sci., 5, 1015 (1965). In the oxotermorine test, groups of 6 mice were injected with 1,3-dihydro-3-(2-hydroxy-2-methylpropyl)-2H-isoindol-1-one (25 and 100 mg/kg, i.p.) or atropine (2 and 5 mg/kg. i.p., calculated as base) 30 min before the intraperitoneal injection of oxotremorine fumarate (0.5 mg/kg, calculated as base). Rectal temperature was measured with a YSI telethermometer 402 physiological probe before administration of test compounds and oxotremorine and at 15 and 30 min after oxotremorine. At the same time the degree of tremor, salivation and lacrimation was scored as follows: 2=strong; 1=weak; 0=none. Results are given in Table 5.

I claim:

1. A method of treating ulcers in a mammal, which comprises orally or parenterally administering to said mammal an effective ulcer alleviating amount of 1,3-dihydro-3-(2-hydroxy-2-methylpropyl)-2H-isoindol-1-one.

2. A method according to claim 1, wherein said effective ulcer alleviating amount is from about 1.0 mg to about 200 mg per kg of body weight per day.

3. An anti-gastric pharmaceutical composition, which comprises an effective amount of 1,3-dihydro-3-(2-hydroxy-2-methylpropyl)-2H-isoindol-1-one and pharmaceutically acceptable carrier therefor.

4. A method for preventing or decreasing the secretion or availability of excessive amounts of gastric acid in a mammal, which comprises administering orally or parenterally to said mammal, suffering from hyperchlorhydria and/or associated conditions, an effective amount of 1,3-dihydro-3-(2-hydroxy-2-methylpropyl)-2-isoindol-1-one.

5. A method according to claim 4, wherein said effective amount is from about 1.0 mg to about 200 mg per kg of body weight per day.

* * * * *

TABLE 5
Oxotremorin-Induced Syndrome

| Treatment | Dose (mg/kg i.p.) | Temperature °C. Before Compounds | Temperature °C. Before Oxotremorine | 15 min T | 15 min S | 15 min L | 15 min Temp | 30 min T | 30 min S | 30 min L | 30 min Temp |
|---|---|---|---|---|---|---|---|---|---|---|---|
| Saline | — | 36.7 ± 1.8 | 36.6 ± 0.3 | 1.9 | 1.8 | 1.8 | 31.0 ±0.2* | 1.9 | 1.8 |  | 28.7 ± 0.2* |
| Isoindol-1-one[a] | 25 | 36.1 ± 0.2 | 36.7 ± 0.2 | 2.0 | 2.0 | 2.0 | 31.4 ±0.2 | 2.0 | 2.0 |  | 29.2 ± 0.2 |
| Atropine | 5 | 36.8 ± 0.3 | 37.2 ± 0.3 | 0.16 | 0 | 0 | 36.9 ±0.2** | 0 | 0.16 |  | 36.9 ± 0.3** |
| Saline | — | 37.0 ± 0.2 | 36.9 ± 0.3 | 2.0 | 1.8 | 1.5 | 31.6 ±0.5* | 1.8 | 1.8 |  | 29.5 ± 0.5* |
| Isoindol-1-one[a] | 100 | 36.1 ± 0.2 | 32.8 ± 0.2* | 2.0 | 2.0 | 0.7 | 31.2 ±0.1 | 2.0 | 1.0 |  | 30.5 ± 0.2 |
| Atropine | 2 | 37.7 ± 0.2 | 37.6 ± 0.2 | 0 | 0 | 0 | 36.7 ±0.4*⁴ | 0 | 0 |  | 35.7 ± 0.4** |

Mice were injected intraperitoneally with test compounds or saline 30 min before oxotremorine. Temperatures were measured before test compound, saline and oxotremorine and 15 and 30 min after the latter drug. Tremor (T), salivation (S), and lacrimation (L) were scored as follows: 2 = strong, 1 = weak, 0 = none.
Each value is mean of 12 mice for saline and 6 mice for compound-treated groups.
**p<0.001 versus control group (Student's-t-test)
*p<0.001 versus oxotremorine group
[a] 1,3-dihydro-3-(2-hydroxy-2-methylpropyl)-2H-isoindol-1-one